(12) United States Patent
Nagayama

(10) Patent No.: US 7,419,833 B2
(45) Date of Patent: Sep. 2, 2008

(54) METHOD FOR NUCLEIC ACID SEQUENCING

(75) Inventor: Kuniaki Nagayama, Aichi Prefecture (JP)

(73) Assignee: Nagayama IP Holdings LLC, New York, NY (US)

( * ) Notice: Subject to any disclaimer, the term of this patent is extended or adjusted under 35 U.S.C. 154(b) by 246 days.

(21) Appl. No.: 10/424,682

(22) Filed: Apr. 28, 2003

(65) Prior Publication Data

US 2004/0038261 A1 Feb. 26, 2004

(51) Int. Cl.
*G01N 33/00* (2006.01)
*G01N 33/53* (2006.01)
*C12Q 1/68* (2006.01)
*C12M 1/34* (2006.01)
*C07H 21/02* (2006.01)
*C07H 21/04* (2006.01)
*C07H 21/00* (2006.01)

(52) U.S. Cl. .................. 436/94; 435/6; 435/287.2; 536/23.1; 536/24.3; 536/25.32; 436/801

(58) Field of Classification Search .......... 435/6, 435/287.2; 436/94, 800
See application file for complete search history.

(56) References Cited

U.S. PATENT DOCUMENTS

| | | | |
|---|---|---|---|
| 5,472,881 A * | 12/1995 | Beebe et al. | 436/94 |
| 5,674,743 A | 10/1997 | Ulmer | 435/287.2 |
| 6,210,891 B1 | 4/2001 | Nyren et al. | 435/6 |
| 2002/0011566 A1 | 1/2002 | Nagayama et al. | 250/311 |
| 2002/0086317 A1 | 7/2002 | Nagayama | 435/6 |

FOREIGN PATENT DOCUMENTS

| | | |
|---|---|---|
| JP | 11258057 | 9/1999 |
| WO | WO 99/09217 | 2/1999 |
| WO | WO 00/06770 | 2/2000 |

OTHER PUBLICATIONS

Whiting, et al., "An Adenine-Specific Stain for DNA Sequencing by Electron Microscopy" Biophys. L, vol. 15 Abstract only, 2001.*
Allemand et al., "ph-Dependent Specific Binding and Combing of DNA" Biophys. J. 73:2064-2070, 1997.
Danev et al., "Transmission Electron Microscopy with Zernike Phase Plate" Ultramicroscopy 88:243-252, 2001.
Demers et al., "Direct Patterning of Modified Oligonucleotides on Metals and Insulators by Dip-Pen Nanolithography" Science 296:1836-1838, 2002.
Kawahara et al., "Ab Initio and Density Functional Studies of Substituent Effects of an A-U Base Pair . . . " J. Phys. Chem. 103:8516-8523, 1999.
Kawahara et al., "Ab Initio Evaluation of the Substitution Effect of the Hydrogen Bond Energy of the Watson . . . " J. Phys. Chem. 105:3894-3898, 2001.
Kawahara et al., "Theoretical Study of the Hydrogen Bond Energy of Base Pairs Formed Between Substituted 1-Methylcytosine . . . " J. Phys. Chem. 105:10596-10601, 2001.
Kawahara et al., "An Ab Initio Study of the Hydrogen Bond Energy of Base Pairs Formed Between Substituted 9-Methylguanine . . . " J. Phys. Chem. 106:3207-3212, 2002.
Li, et al., "Multiple Thiol-Anchor Capped DNA-Gold Nanoparticle Conjugates" Nucleic Acids Res. 30(7):1558-1562, 2002.
Moudrianakis et al., "Base Sequence Determination in Nucleic Acids with the Electron Microscope, III . . . " Proc. Nat'l. Acad. Sci. USA 53:564-571, 1965.
Namasivayam et al., "Electrostretching DNA Molecules Using Polymer-Enhanced Media within Microfabricated Devices" Anal. Chem. 74:3378-3385, 2002.
Beer et al., "Determination of Base Sequence in Nucleic Acids with the Electron Microscope:" Biochemistry vol. 48:409-416, 1962.
Gal-Or, et al., "Electron Microscope Study of Base Sequence in Nucleic Acids. VII. Cytostine-Specific Addition of Acyl Hydrazides" Biochemistry vol. 6(7):1909-1915, 1967.
Highton et al., "Electron Microscope Study of Base Sequences in Nucleic Acids. VIII. Specific Conversino of Thymine into Anionic Osmate Esters" Biochemistry vol. 7(2):825-833, 1968.
Leontis et al., "Geometric nomenclature and classification of RNA base pairs" RNA Journal vol. 7:499-512, 2001.
Whiting, et al., "An Adenine-Specific Stain for DNA Sequencing by Electron Microscopy" Biophys. J., vol. 15, Abstract only, 2001.
Kyogoku, et al., Proc. Nat'l. Acad. Sci. USA 57:250-257, 1967.

* cited by examiner

*Primary Examiner*—Bradley L Sisson
(74) *Attorney, Agent, or Firm*—Fish & Richardson P.C.

(57) ABSTRACT

A method for determining the sequence of at least a portion of a single-stranded nucleic acid molecule by base-specifically labeling the exposed bases of the nucleic acid molecule using heavy element-substituted nucleotide bases which form Watson-Crick type base-pairs with the exposed bases of the nucleic acid molecule and then imaging the labeled single-stranded nucleic acid molecule using electron microscopy, e.g., transmission electron microscopy (TEM), or some other method that permits discrimination of the heavy element substituted nucleotide bases is described. The image is analyzed to determine the base sequence of at least a portion of the nucleic acid molecule.

37 Claims, 2 Drawing Sheets

US 7,419,833 B2

METHOD FOR NUCLEIC ACID SEQUENCING

This application claims priority from U.S. application Ser. No. 09/992,538 (U.S. Published Application 2002 0086317 A1) filed Nov. 19, 2001, which application claims priority from Japanese Application 2000-351844 filed Nov. 17, 2000, the entirety of which applications are hereby incorporated by reference.

BACKGROUND OF THE INVENTION

There are a variety of methods for sequencing nucleic acid molecules. Historically, the most common methods have been based on chemical (Maxam and Gilbert sequencing) or enzymatic (Sanger dideoxy sequencing and exonuclease-based sequencing) reactions that create specific truncated nucleic acid molecules that are then separated by electrophoretic techniques in order to determine their relative length. More recently, potentially higher throughput techniques, including pyro-sequencing and hybridization-based sequencing methods, have been developed. It has also been proposed that scanning tunneling microscopy could be used to directly visualize the sequence of a nucleic acid molecule.

SUMMARY OF THE INVENTION

The invention features a method for determining the sequence of at least a portion of a single-stranded nucleic acid molecule by base-specifically labeling the exposed bases of the nucleic acid molecule using heavy element-substituted nucleotide bases which form Watson-Crick type base-pairs with the exposed bases of the nucleic acid molecule and then imaging the labeled single-stranded nucleic acid molecule using electron microscopy, e.g., transmission electron microscopy (TEM), or some other method that permits discrimination of the heavy element substituted nucleotide bases. The image is analyzed to determine the base sequence of at least a portion of the nucleic acid molecule.

To create a suitable image of a portion of a nucleic acid molecule, a single-stranded nucleic acid molecule is placed on a support film, preferably in an elongated state such that the spacing between bases is greater than 0.5 nm (or at least 0.6 or 0.7 nm) and then exposed to one or more base-specific labels that can be discriminated by an appropriate imaging technique such TEM. The base-specific labels are four different modified nucleotide bases (adenine (A), guanine (G), cytosine (C) and thymine (T) or uracil (U)) each of which includes a different heavy element-containing group. These modified nucleotide bases form base-pairs with the exposed bases in the elongated single-stranded nucleic acid molecule according to normal Watson-Crick base pairing rules (A-T or A-U and G-C).

The TEM used for imaging can optionally be equipped with a tilt imaging system. Phase-contrast TEM and complex TEM can also be used for imaging the labeled molecule and distinguishing the heavy element labeled bases based of the intensity of electron scattering. The electron microscope image can be analyzed with software for discriminating heavy elements within the heavy element containing groups. When heavy elements are distinguished using such software, the electron scattering intensity measured by the microscope is used as a basis for quantitative measurement of the heavy metals and thus base identification.

The heavy elements within the heavy element containing groups used to modify the nucleotide bases are preferably metal elements having an electron scattering intensity sufficient to be detected by electron microscopy. For example, metals with an atomic number greater than 25 are suitable for use as heavy elements in the context of the methods of the invention. So that the different modified nucleotide base can be distinguished, each must include a heavy element-containing group that differs in atomic number from the atomic number of the heavy element-containing group of each other modified nucleotide base by about 15. Thus, to obtain four distinguishable heavy element-containing groups, one for each of the four nucleotide bases, it is desirable to use combinations of four different heavy elements having an atomic number greater than, e.g., 25 and differing in atomic number by about 15. Examples of such combinations include: $_{78}$Pt, $_{63}$Eu, $_{46}$Pd, and $_{27}$Co; $_{92}$U, $_{76}$Os, $_{46}$Pd, and $_{26}$Fe; $_{80}$Hg, $_{64}$Gd, $_{48}$Cd, and $_{30}$Zn; and $_{89}$Ac, $_{74}$W, $_{42}$Mo, and $_{25}$Mn. A given heavy element containing group can include two or more (2, 3, 4, 5, 6, 7, 8, 9, 10, or more) heavy element atoms and within a single group the two or more elements can be the same or different. Where a heavy element containing group contains multiple atoms, it is the total atomic number of the heavy elements in a given group that preferably differs from the total of those in each other base specific label by about 15.

The labeled nucleic acid molecule is imaged and the image is analyzed to identify the order of the base-specific labels and thus determine the base sequence of at least a portion of the molecule. To facilitate analysis of the images, at least a portion the nucleic acid molecule is preferably elongated when molecule is imaged. This can be best achieved by placing the molecule on the support film in an elongated state. In cases where the nucleic acid molecule is not fully elongated, e.g., where the molecule includes at least one loop formed by the nucleic acid backbone crossing over itself, multiple images at different tilt angles are obtained using, for example, an optional tilt imaging system. In this manner it is possible to collect depth information. Imaging processing techniques are then used to follow the backbone and thus determine the order of bases in the nucleic acid molecule.

In one example, heavy element-substituted A is labeled with palladium (atomic number 46), a heavy element-substituted C is labeled with europium (atomic number 63), a heavy element-substituted G is labeled with platinum (atomic number 78), and a heavy element-substituted U is labeled with cobalt (atomic number 27). These four heavy element labeled bases are exposed to a single-stranded nucleic acid molecule (DNA or RNA) on a support surface. The heavy element-substituted base selectively form base-pairs with T (or U), G, C, and A in the single stranded nucleic acid molecule. Non-base-paired heavy element labeled bases are washed away. The heavy elements in the remaining labeled nucleotides act as reporters that can be discriminated by TEM. Thus, if a platinum atom is discerned on a TEM image at a given position, this means that the Pt-labeled G is present at that position and that the corresponding base of single-chain DNA is C. The other three bases can be similarly identified by discerning the electron scattering of their respective metal atoms.

The invention features a method for determining the sequence of a plurality of bases in a nucleic acid molecule, comprising: (a) providing a support surface bearing a single stranded nucleic acid molecule comprising a plurality of bases labeled with one of four different base-specific labels; (b) detecting the base-specifically labeled bases by electron microscopy; and (c) analyzing the detected base-specifically labeled bases to determine the sequence of the nucleic acid molecule.

In various embodiments: each base-specific label comprises at least one atom having an atomic number greater than 25; each bases is labeled with one of four base-specific labels, wherein each of said four base-specific labels comprises a different element having an atomic number greater than 25 and each element having an atomic number greater than 25 differs in atomic number from each other element having an atomic number greater than 25 by an atomic number of at least 15; the elements are selected from the group consisting of: Pt, Eu, Pd, Co, U, Os, Fe, Hg, Gd, Cd, Zn, Ac, W, Mo, and Mn; and the four base-specific labels consist of: (i) a label comprising a substituted adenine, (ii) a label comprising a substituted uracil or a substituted thymine, (iii) a label comprising a substituted cytosine, and (iv) a label comprising a substituted guanine. The bases are not substituted at the positions involved Watson-Crick base-pairing, i.e., the groups normally found at these positions in the bases are present.

In certain embodiments the four elements used in are: (i) Pt, Eu, Pd, and Co; (ii) U, Os, Pd and Fe; (iii) Hg, Gd, Cd and Zn; or (iv) Ac, W, Mo and Mn.

In various embodiments: N7 or N9 of the substituted adenine is substituted with a group comprising an element having an atomic number greater than 25; N7 or N9 of the substituted guanine is substituted with a group comprising an element having an atomic number greater than 25; N1 of the substituted cytosine is substituted with a group comprising an element having an atomic number greater than 25; N1 of the substituted uracil is substituted with a group comprising an element having an atomic number greater than 25; N1 of the substituted thymine is substituted with a group comprising an element having an atomic number greater than 25; the substituted adenine has a substitution that increases the specificity of Watson-Crick type base-pairing with uracil or thymine; the substituted thymine or substituted uracil has a substitution that increases the specificity of Watson-Crick type base-pairing with adenine; the substituted cytosine has a substitution that increases the specificity of Watson-Crick type base-pairing with guanine; the substituted guanine has a substitution that increases the specificity of Watson-Crick type base-pairing with cytosine; the substituted adenin is substituted at C2 or C8 or both C2 and C8; the substituted thymine or the substituted uracil has a substitution at C5 or C6 or both C5 and C6; the substituted cytosine or the substituted uracil has a substitution at C5 or C6 or both C5 and C6; the substituted guanine is substituted at C2; and the modification is a substituted or unsubstituted alkyl group or a halogen.

In various embodiments: the 3' nucleotide or the 5' nucleotide of the nucleic acid molecule is covalently bound to a defined region of the support surface; the defined region of the support surface is coated with gold; the support surface bears a plurality of single-stranded nucleic acid molecules wherein the 3' nucleotide or the 5' nucleotide of each nucleic acid molecule is covalently bound to a defined region of the support surface; the plurality of nucleic acid molecules form a regular array; and each of the plurality of single-stranded nucleic acid molecules is covalently bound to a different defined region of the support surface.

In certain embodiments: each base-specific label comprises at least 2 atoms having an atomic number greater than 25; and each base-specific label comprises a group selected from the group consisting of: $B_{10}I_9COOH$, $C_2B_{10}I_{10}$, $C_2B_{10}Br_{10}$, $C_2B_{10}Cl_{10}$, $C_2B_{10}F_{10}$.

In certain embodiments: the electron microscopy is transmission electron microscopy; the transmission electron microscopy includes the use of a transmission electron microscope comprising a Zernike phase plate located behind the objective lens; and the electron microscopy comprises the use of a complex electron microscope.

The invention also features a method for determining the sequence of a plurality of bases in a nucleic acid molecule, comprising: (a) providing a support surface bearing a single stranded nucleic acid molecule comprising a plurality of bases; (b) contacting the single stranded nucleic acid molecule with four different base-specific labels in the presence of an organic solvent that is free of hydrogen bond donors and acceptors to allow non-covalent binding of the four different base-specific labels to the plurality of bases; (c) detecting the base-specifically labeled bases by electron microscopy; and (d) analyzing the detected base-specifically labeled bases to determine the sequence of the nucleic acid molecule.

The invention also features: a substituted adenine wherein the C2 or C8 position is substituted with a $C_1$-$C_5$ alkyl group or a halogen and the N7 or N9 position is substituted with a group comprising an element having an atomic number greater than 25; a substituted guanine wherein the C8 position is substituted with a $C_1$-$C_5$ alkyl group or a halogen and the N7 or N9 position is substituted with a group comprising an element having an atomic number greater than 25; a substituted uracil wherein the C5 or C6 position is substituted with a $C_1$-$C_5$ alkyl group or a halogen and the N1 position is substituted with a group comprising an element having an atomic number greater than 25; and a substituted cytosine wherein the C5 or C6 position is substituted with a $C_1$-$C_5$ alkyl group or a halogen and the N1 position is substituted with a group comprising an element having an atomic number greater than 25.

In various embodiments the element having an atomic number greater than 25 is selected from the group consisting of: Pt, Eu, Pd, Co, U, Os, Fe, Hg, Gd, Cd, Zn, Ac, W, Mo, and Mn.

DETAILED DESCRIPTION

Figure 1:
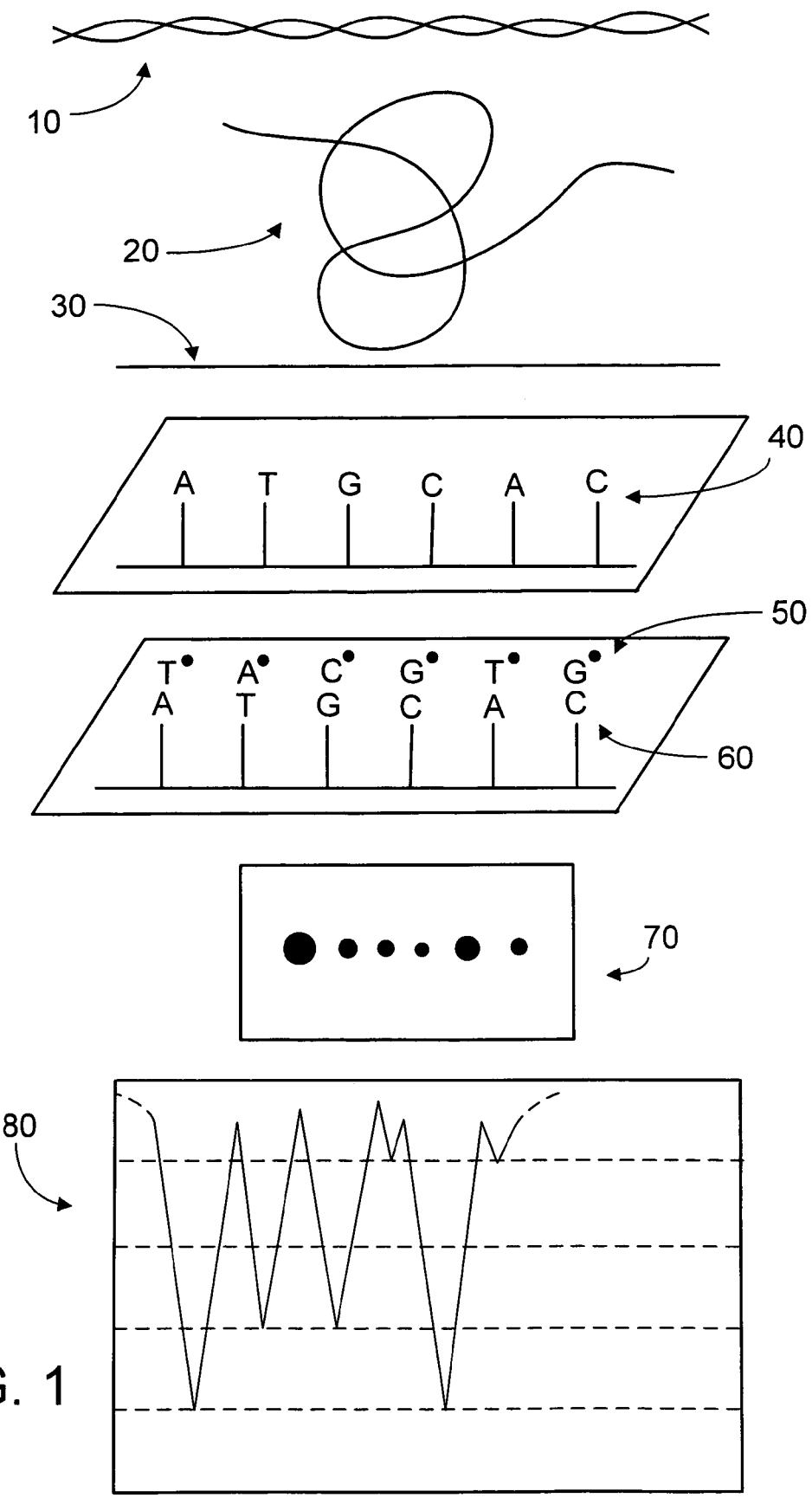
FIG. 1 is a schematic depiction of the sequencing of a portion of a nucleic acid molecule according to one embodiment of the invention.
Figure 2:
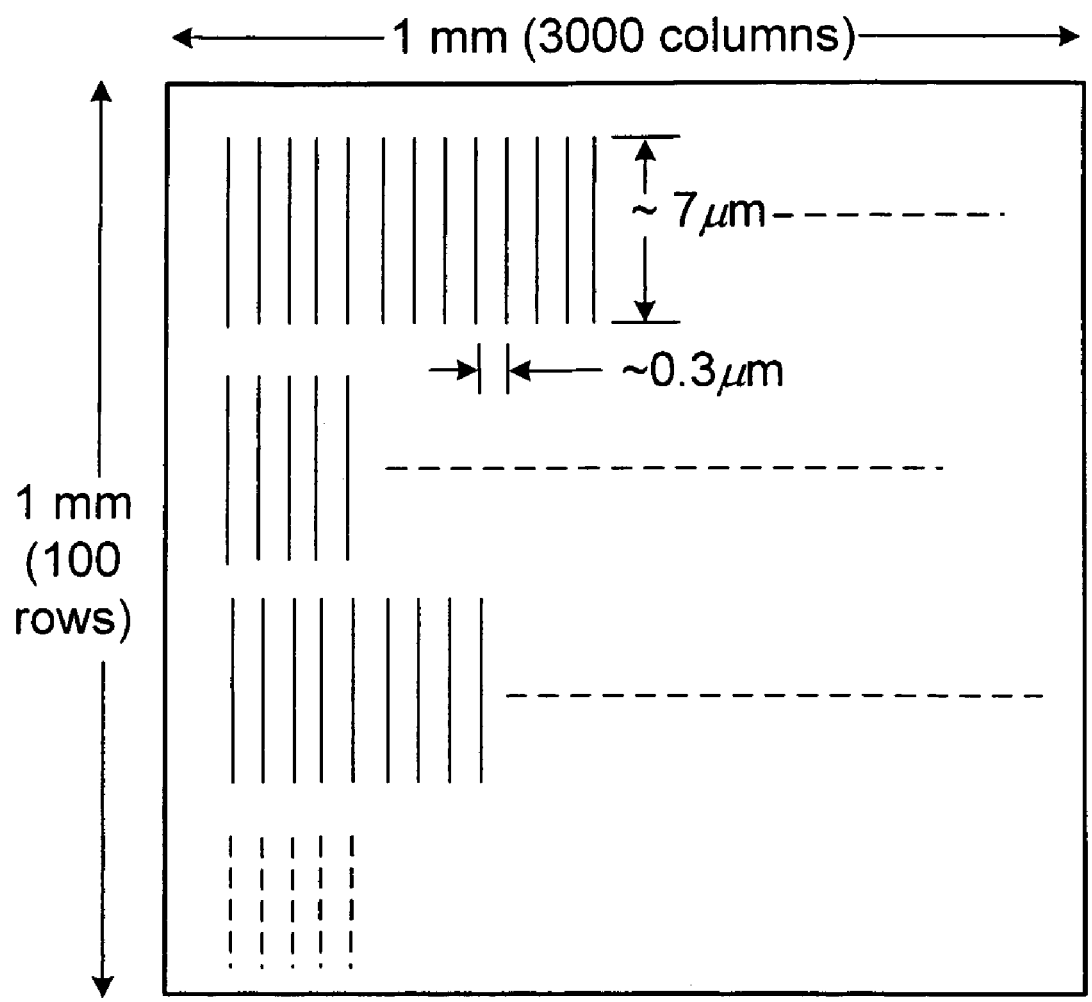
FIG. 2 is a schematic depiction of a support holding an array of elongated nucleic acid molecules.

FIG. 1 is a schematic depiction of the sequencing of a portion of a nucleic acid molecule according to one embodiment of the invention. A DNA molecule is obtained 10. The molecule is denatured to obtain a single strand 20. This single strand is converted to an elongated form 30 that is placed on a thin film support 40. The elongated molecule on the support is exposed to heavy element labeled nucleotide bases (A°, T°, G° and C°) 50 which selectively base pair to exposed bases 60 in the elongated molecule. TEM is used to image the resulting base-specifically labeled molecule and the heavy element labeled nucleotide bases appear as a series of spots of varying intensity depending on the atomic number of the heavy element present in the heavy element labeled nucleotide base 70. The image is analyzed 80 to determine the intensity of spots and thus the order of bases in the nucleic acid molecule.

Preparation of a Support Bearing an Elongated Nucleic Acid Molecule

The nucleic acid molecule being analyzed is placed on a specimen support suitable for imaging by electron microscopy (i.e., an EM or TEM grid). The support should be selected to avoid background noise problems associated with background shot noise and fog generated by the support. Background shot noise can be reduced by increasing the electron beam dose and fogging can be reduced by using a thin support. The specimen support is preferably a thin film that firmly holds single-stranded nucleic acid molecules, is robust enough to withstand intense electron beam irradiation, and is made of a light element that does not significantly scatter the electron beam used by the EM or TEM.

Carbon thin film and aluminum thin film can be used to hold nucleic acid molecules for EM or TEM imaging. However, these films can produce strong background fog. In addition, these films tend to decrease the contrast of labeling heavy elements bonded as base pairs. Organic support films made of lipids or denatured natural proteins (e.g., albumin and casein) or synthetic artificial proteins (e.g., polylysine) are generally more useful. Once a support film has been prepared, it is transferred to TEM grid.

There are a number of suitable approaches from binding and elongating nucleic acid molecules that have been attached at one end to a surface. For example, a coverslip can be placed over a liquid droplet containing the attached DNA molecule. As the droplet dries, the meniscus recedes stretching the nucleic acid molecule perpendicular to the meniscus (Bensimon et al. 1995 *Phys. Rev. Lett*. 74:4754). Alternatively, the Langmuir-Blodgett film method may be employed. Here, the surface bearing the nucleic acid molecule is slowly withdrawn from a buffer and then slowly pulled from the buffer (Michalet et al. 1997 *Science* 277:1518). Other elongation methods that are useful include: electric stretching (2002 *Ultramicroscopy* 91:139) and spin-stretching (Yokota et al. 1999 *Anal. Chem*. 71:4418).

An unmodified nucleic acid molecules can be bound at one end to many surfaces. example, when a nucleic acid molecule in pH 5.5 MES (2-[N-morpholino]ethanesulfonic acid) buffer is applied to a surfaces coated with silane possessing a vinyl end group, one or both ends of the molecule spontaneously bind to the surface. In general, end binding (as opposed to binding internally) occurs over a narrow pH range (about 0.2 units on hydrophobic surfaces such as polystyrene, Teflon and graphite) with the optimum pH on hydrophobic surfaces commonly being near pH 5.5 (Allemand et al. 1997 *Biophysical Journal* 73:2064).

A nucleic acid molecule with a thiol group at one end will bind to gold. This method is described, for example, in U.S. Pat. No. 5,472,881 (see also Rongchao et al. 2002 *Nucl. Acids. Res*. 30:1558 and 1993 *FEBS Lett*. 336:452). Alkylthiol- or disulfide-terminated nucleic acid molecules can be directly adsorbed to gold. The nucleic acid molecule can be derivatized at either end so that both 5' and 3' immobilization is possible. Specific binding is achieved by simply exposing the thiolated nucleic acid molecule suspending in buffer to the gold surface. This technique can be combined with electrostretching techniques to obtain elongated nucleic acid molecules affixed at one end to a gold anchor (Namasivayam et al. 2002 *Anal. Chem*. 74:3378).

Modification of Bases to Improve Organic Solvent Solubility and Base-pairing Specificity Base-specific labeling is achieved using standard nucleotide bases or derivatives thereof that are attached to a heavy element containing group. To increase the specificity of base-pair formation, the nucleotide bases or derivatives thereof are exposed to the single stranded nucleic acid molecule on an organic solvent. This is because an aqueous solvent will compete for the hydrogen bonding sites and disrupt base-pair formation.

Nucleotide base derivatives that have increase solubility in an organic solvent or that form bases pairs with higher specificity are useful in the methods of the invention. The four nucleotide bases are depicted below to facilitate understanding of the modification of the bases. Formula I is adenine (A). Formula II is uracil (U). Formula III is guanine (G). Formula IV is cytosine. Thymine is identical to uracil expect that there is a methyl group at position C5 rather than an H.

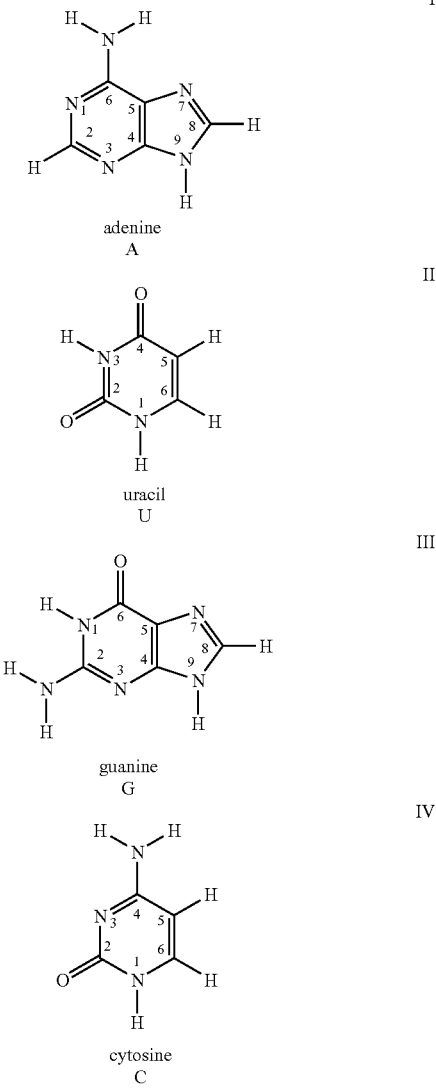

Because the base-pairing takes place in a organic solvent, the modified bases must be soluble in an organic solvent. Modifications of A at 2- and 8-positions, G at 8-position, and U, C at 5- and 6-positions will increase solubility in organic solvent. Halogenation and alkylation are useful both for improving the selectivity of pair bonding and increasing solubility in organic solvents. Modification with a hydrophobic alkyl group at a position where base-pair bonding is not hindered is desirable for increasing organic solvent solubility. Examples of the modifying group include ethyl groups, propyl groups, and cyclohexyl groups. Halogen and alkyl groups contribute to both improvement of dissolubility into organic solvents and improvement of the selectivity of pair bonding formation. Improvement of solubility in organic solvents can also be accomplished by introducing an alkyl group or the like to nitrogen atom at 7- or 9-position of A or G and to nitrogen atom at 1-position of U or C. In addition, a heavy element complex that is used for labeling may promote solubility into an organic solvent depending on the design. To achieve higher solubility in an organic solvent a base can be partially substituted by at least one substituent group selected from the group consisting of alkyl groups, cyclohexyl groups, halogen groups, phenyl groups, and phenol groups. In the case of adenine (A), the substituent group is located at the 2- and/or 8-positions. In the case of guanine (G), the substituent group is located that the 8-position. In cases of uracil (U) and cytosine (C), the substituent group is located at the 5- and/or 6-positions. Where two substituent groups are used, they can be identical, similar or dissimilar in kind.

Formula V depicts an U-A Watson-Crick type base-pair. Formula VI depicts an C-G Watson-Crick type base-pair.

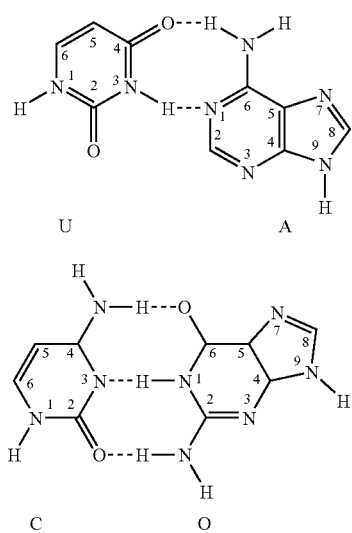

Modified bases can be used to increase the specificity of base-pairing, e.g., to reduce the formation of G-G, G-A, or G-U base-pairs relative to the appropriate G-C base-pair. Modification can also decrease the occurrence of non-Watson-Crick base-pairing, i.e., it can reduce the formation of Hoogstein type base-pairs. To increase specificity, A, U, G, and C can be are modified with halogens (e.g., Cl, Br and I), methyl groups, ethyl groups, alkyl groups (such as cyclohexyl groups), amino groups, or the like. Modification sites can be 2- and 8-positions for A, 8-position for G, and 5- and 6-positions for U and C. For example, halogenation of A and G at 8-position, animation of A at 2-position, and halogenation of U and C at 5-position intensify pair bonding and enhance the selectivity.

The substituents at the 2-position and 8-position in A, the 8-position in G, and the 2-position and 5-position in U (T) and C include: halo, substituted or unsubstituted $C_1$-$C_{12}$ alkyl, substituted or unsubstituted $C_3$-$C_{10}$ cycloalkyl, substituted or unsubstituted $C_2$-$C_{12}$ alkenyl, substituted or unsubstituted $C_5$-$C_{12}$ cycloalkenyl substituted or unsubstituted $C_2$-$C_{12}$ alkynyl, amino, and —NH($C_1$-$C_6$ alkyl).

As used herein, the term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl).

The term "cycloalkyl" as employed herein includes saturated cyclic, bicyclic, tricyclic, or polycyclic hydrocarbon groups having 3 to 12 carbons, wherein any ring atom capable of substitution can be substituted by a substituent. Examples of cycloalkyl moieties include, but are not limited to, cyclopentyl, norbornyl, and adamantyl.

The term "cycloalkenyl" as employed herein includes partially unsaturated, nonaromatic, cyclic, bicyclic, tricyclic, or polycyclic hydrocarbon groups having 5 to 12 carbons, preferably 5 to 8 carbons, wherein any ring atom capable of substitution can be substituted by a substituent. Examples of cycloalkyl moieties include, but are not limited to cyclohexenyl, cyclohexadienyl, or norbornenyl.

The term "substituents" refers to a group "substituted" on an alkyl, cycloalkyl, alkenyl, alkynyl, heterocyclyl, heterocloalkenyl, cycloalkenyl, aryl, or heteroaryl group at any atom of that group. Suitable substituents include, without limitation, alkyl, alkenyl, alkynyl, alkoxy, acyloxy, halo, hydroxy, cyano, nitro, amino, $SO_3H$, sulfate, phosphate, perfluoroalkyl, perfluoroalkoxy, methylenedioxy, ethylenedioxy, carboxyl, oxo, thioxo, imino (alkyl, aryl, aralkyl), $S(O)_n$ alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

Useful modified bases include: 8-bromopurine, 2,6-diaminopurine, 5-bromouracil, 5-iodouracil, and 5-alkyluracil. Introducing a methyl group into 5-position of uracil to enhance the selectivity of base-pair formation gives rise to nothing other than thymine. Accordingly, thymine derivatives are also embraced in the uracil derivatives in accordance with the present invention.

Base-pairing Conditions

The heavy-element labeled bases and the single-strand nucleic acid molecules are brought into contact in the presence of an organic solvent, preferably an organic solvent that lacks hydrogen bond donors and acceptors. Polar solvents that are ionic liquids and have a relatively high dielectric constant and lack hydrogen bond donors or acceptors will readily solubilize heavy-element labeled bases and will not interfere with base-specific binding. Thus, ionic liquids such as organic salts made of combination of cations (imidazoliums, pyrrolidinums, pyridinums, phosphoniums) and anions (borates, sulfates, sulfonates, amides, imides, halogenides) are useful solvents.

Also useful are organic solvents having a dielectric constant below 10. Such solvents include: chloroform, heptane, cyclohexane, carbon tetrachloride, acetonitrile, aniline, ethyl amine, cresol, acetic acid, trichloroacetic acid, dimethyl ether, diethyl ether, toluene, toluidine, benzylamine, phenol, decanol, benzene, quinoline, morpholine, dimethyl amine, chlorobenzene, dichloromethane, dichloroethylene, tetrahydrofuran, trichloroethylene, dichlorobenzene, fluorobenzene, bromobenzene, pentanol, siloxane, and glyceride. One or more heavy element-labeled bases are dissolved in a solvent or solvent mixture that includes at least one organic solvent and then applied to the nucleic acid molecule attached to the support film. The non-polar or low-polarity organic solvent facilitates specific base-pairing. However, polar solvents, e.g., chloroform, toluene, aniline, and pentanol, are useful for solubilizing the base-specific labels. In general, any suitable relatively non-hydrogen bonding solvent can be used. The preferred solvent or solvent mixture in a given situation will depend on particular base-specific labels used in a given labeling reaction.

Heavy Element Labels

Each of the bases or base derivatives is preferably labeled with a heavy element complex that is resistant to organic solvents and resistant to mass loss events caused due by electron bombardment. For A and G (or A and G derivatives) the heavy element complex is preferably bonded, e.g., covalently, to N7 or N9. For U (or T) and C (or U or T and C derivatives), the heavy element complex is preferably bonded, e.g., covalently, to N1. Of course, it is also possible to link a heavy element containing group at both the N7 and N9 positions of A or G rather than either the N7 position or the N9 position. In this case, the number of heavy element atoms is increased. The resolution and contrast of the TEM image are enhanced thereby allowing for improved base discrimination. Methods for synthesizing nucleotides with heavy metal labels are well-kwon in the art (see, e.g., Moudrianakis and Beer, 1965 *Proc. Natl. Acad. Sci. USA* 53:564; Beer et al. 1978/1979 *Chemica Scripta* 14:263; and Commerford 1993 *Biochemistry* 10:1993).

Suitable heavy element complexes include amine complexes, benzene complexes, metallocene complexes, olefin complexes, and many other complexes. When a heavy element complex is bonded to a base, it can be a heavy element complex obtained by coordinating a metal element directly to nitrogen within a base. Furthermore, a heavy element complex may be bonded to nitrogen within a base via a so-called linker or adapter, such as a polymethylene chain or polyoxyalkylene chain.

The heavy element complex preferably includes a metal that has an electron scattering intensity sufficient to be detected by techniques such as TEM. Thus, the heavy element complex preferably includes at least one metal atom with an atomic number greater than 25, preferably greater than 30. Suitable metal atoms includes: Pt, Eu, Pd, Co, U, Os, Fe, Hg, Gd, Cd, Zn, Ac, W, Mo, and Mn. Since it is important that each of the four different labeled bases be distinguishable by electron microscopy or the like, the metal atom used in each of the four different labeled bases preferably differ in atomic number by at least 10, 11, 12, 13, 14, 15, 16, 17, 18, 19, 20, 25 or more. Any combination of the metal atoms differing sufficiently atomic number can be used for the four different labeled bases. Suitable combinations include: Pt, Eu, Pd and Co; U, Os, Pd and Fe; Hg, Gd, Cd and Zn; and Ac, W, Mo and Mn. Any metal can be used in combination with any bases so long as the four metals differ sufficiently in atomic number.

The heavy element complex used in the present invention is not limited to heavy element complexes where each molecule includes one metal atom. A complex including plural metal atoms can also be used. The use of these complexes is more desirable in terms of discrimination between elements or atoms and discrimination of signal from noise. One example of such complexes including plural metal atoms is a disubstituted heavy element complex in which one molecule contains two metal atoms. Another example is a trisubstituted complex containing three metal atoms. A further example is an iron-sulfur cluster-metal complex including four metal atoms. The atoms included in one complex may be similar or dissimilar metal elements.

For the discrimination of bases based on the total atomic number, the partial substitution of bases by heavy halogen atoms, such as iodide and bromide, can be used. For example, the following labels are readily detectable: $B_{10}I_9COOH$, $C_2B_{10}I_{10}$, $C_2B_{10}Br_{10}$, $C_2B_{10}Cl_{10}$, $C_2B_{10}F_{10}$.

It should be noted that if a base with high frequency is combined with a lighter element or if a base with low frequency is combined with a heavier element, mutual interference is reduced. Examples of these combinations include: adenine-Pd, guanine-Pt, cytosine-Eu, uracil-Co and adenine-Zn, guanine-Hg, cytosine-Gd, uracil-Cd.

Formula VII depicts a Pd labeled A base-paired with a T in the single-stranded nucleic acid molecule.

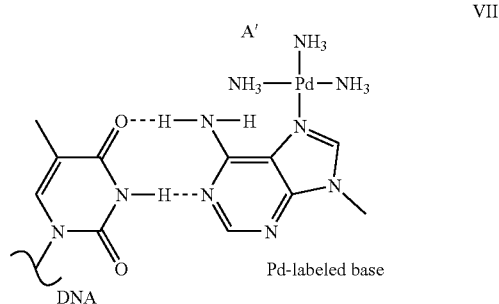

VII

Formula VIII depicts an Eu labeled C based-paired with a G in the single stranded nucleic acid molecule.

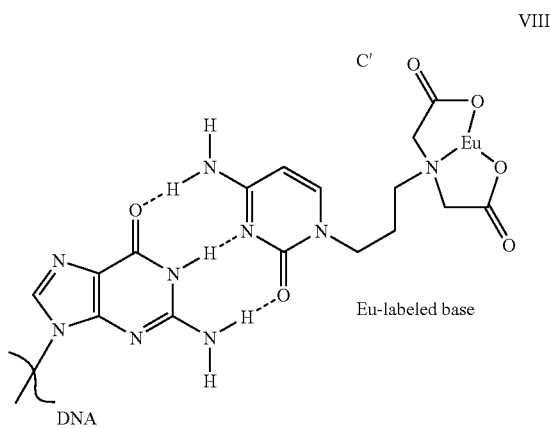

VIII

Formula IX depicts Depicted below is a Pt labeled G based-paired with a C in the single stranded nucleic acid molecule.

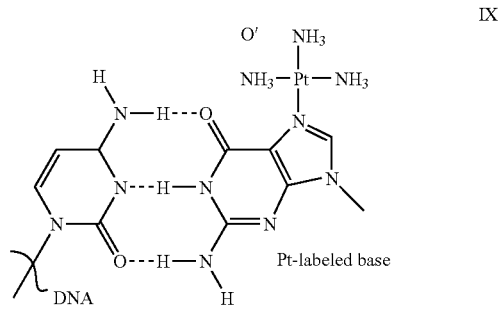

IX

Formula X depicts Depicted below is a Co labeled U based-paired with an A in the single stranded nucleic acid molecule.

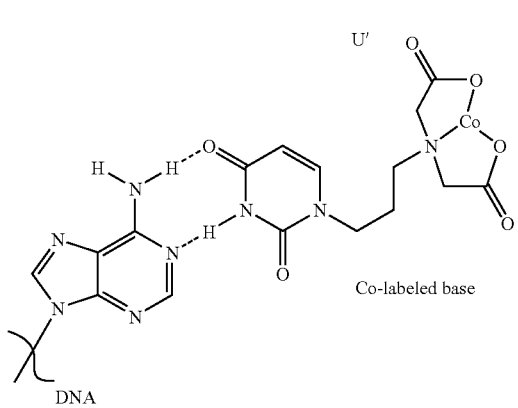

Co-labeled base

Heavy element clusters can be used for base-specific labeling. Using such clusters increases image contrast thereby increasing the sensitivity and reliability of base discrimination. Since the clusters are quite large, lower resolution imaging methods can be used. For example, a low voltage (e.g., 100 kV) phase-contrast electron microscope can provide adequate resolution. Suitable heavy element clusters include naturally occurring iron-sulfur clusters and their metal substitutes. For example, in a cubic iron-sulfur cluster (cubane) iron and sulfur atoms are alternately coordinated at the eight vertices of a cube creating a cluster having four heavy atoms.

Many heavy element clusters are unstable in water. However, they do exist in complexed to proteins, e.g., in ferredoxin and hydrogenase. Heavy element clusters are generally stable in organic solvents. Thus, bases labeled with heavy element clusters are stable if exposed only to organic solvents. The clusters can be attached to bases directly or via a linker or adapter. The use of heavy element clusters provides many options for creating base-specific labels since the relevant atomic number difference between any two labels is the total atomic number of the heavy elements in each cluster. For example the relevant atomic number of a cluster having two Fe atoms (atomic number 26) and two Mo atoms (atomic number 42) is 136 (2×26+2×42).

Formula XI depicts a cysteine-complexed heavy metal cluster.

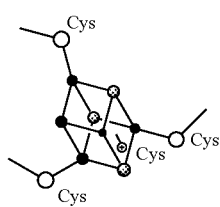

The stability of G-C base-pairs between unsubstituted C and G substituted at N9 might be improved by substitution of C8 or the C2 amino group of G with an electron withdrawing group, e.g., $NO_2$, O (oxo), F, (particularly at or COH (formyl)

Imaging

An electron microscope that can achieve sufficient contrast and resolution to perform quantitative elemental analysis of one atom of a heavy element with an atomic number greater than about 25 can be used to image the labeled nucleic acid molecule. The system should be capable of quantitative detection of two elements that differ in atomic number by 35 or less, preferably 30, 25, 20, 15 or less.

Commercially available TEM and enhanced versions of TEM are useful for imaging the labeled nucleic acid molecules. Phase contrast TEM is particularly useful in the methods of the invention. Phase contrast TEM can be achieved in several ways. For example, the objective lens can be defocused, allowing only a portion of the spatial frequency components in the exit wave to be expressed in the image (Scherzer (1949) *J. Appl. Phys.* 20:20). In this approach the resulting loss of low spatial frequency components (e.g., image alignment, low frequency object information, and particle finding) is compensated for by taking a series of defocused images and numerical reconstructing the object phase (Kirkland 1984 *Ultramicroscopy* 15:151 and Coene et al. 1992 *Phys. Rev. Lett.* 69:3743). Alternatively, energy filtering can be used to remove the inelastic contributions to the images thereby achieving higher contrast and a better signal-to-noise ratio for the low frequency components (Schroder et al. 1990 *J. Struct. Biol.* 105:28).

More recently phase contrast TEM has been achieved using a Zernike phase plate positioned in the back-focal plane of the objective lens. The phase plate is a thin material film having a center hole. Unscattered electrons pas through the hole, while scattered electrons pass through the thin films are phase retarded. A suitable phase plate can be prepared by vacuum evaporation of carbon on to freshly cleaved mica. The film is floated on water and transferred onto a molybdenum objective lens aperture. The opening in the center of the phase plate can be produced using a ion beam. For a $-i/2$ phase shift, a 31 nm thick carbon film can be used for the acceleration voltage of 300 kV and a 24 nm carbon thick film can be used for an acceleration voltage of 100 kV (see Danev and Nagayama 2001 *Ultramicroscopy* 88:243-252 and Japanese Patent Application No. 2000-085493). To achieve a high resolution (0.2 to 0.3 nm) permitting discrimination between heavy elements, the TEM preferably has low spherical aberration and chromatic aberration thereby achieving a high resolution limit. A high-resolution and high-contrast TEM that permits insertion of a phase plate and is capable of discriminating between individual atomic elements preferably uses a voltage of more than 300 kV. In the case of discrimination between element clusters each made up of 3 to 5 atoms, lower voltage, for example, a 100 kV TEM.

A complex electron microscope that combines a phase-contrast TEM and a standard TEM can be used to achieve resolution of 0.2 to 0.3 nm (Japanese Patent Publication No. 11-258057). For example, a complex electron microscope image consisting of a real number component signal and an imaginary number component signal is obtained by detecting the real number component TEM image of a specimen and the imaginary number component TEM image produced by phase-shifting only electron waves transmitted through the specimen by i/2 and taking the complex sum of the real number component TEM image and the imaginary number component TEM image.

Independently of the above-described methods, improved contrast TEM can be achieved using a cryogenic specimen stage. The use of such a stage allows one to increase the electron dose which increases the signal to noise ratio.

Image Analysis

Images generated by TEM are recorded and processed as digital information by a computer which can identify heavy elements by signal intensity. The recording medium used for image analysis is selected to be appropriate for the magnified image produced by the TEM.

Assuming one base occupies an area of 0.7 nm×0.7 nm within the TEM image and that an allowance that is 10 times the occupied area is given to the TEM image for reliable discrimination between bases and that $10^5$ bases are captured in a single image, then one frame of an image has an actual area of $0.7 \times 0.7 \times 10^5$ nm$^2$ or about 0.5 îm$^2$. If each pixel is set to half the resolution (e.g., 0.15 nm), then the number of required pixels is $(0.7 \times 10^3 \text{ nm}/0.15 \text{ nm})^2$ or about $2 \times 10^7$. Thus, digital recording media such as CCDs and imaging plates (IPs) can be used for image capture. However, the size per pixel is preferably substantially equal to the pixel size of about 5 îm of high-resolution photographic film.

The present analysis system is characterized in that it can analyze the sequence of single-stranded nucleic acid molecules even if the backbone is not completely elongated. For example, the sequence of a nucleic acid molecule can be determined even when the backbone is bent or has portions which appear to touch each other or if the backbone crosses over itself, forming an intersection. If the base spacing between chain portions close to an intersection is relatively large, the bases can be discriminated based on the atomic number dependence intensity of the spot observed while tracing the backbone. Thus, the sequence can be determined.

If the intersection created by backbone crossing is such that the backbone cannot be readily traced, two or more images of the intersection region are collected. The sample is tilted differently, for example by about 30°, for each image. In this manner depth information is obtained, and an image from which overlap has been removed is derived.

Arrays

The nucleic acid sequencing method is suited to very high through-put analysis. As discussed above, this is because the method does not depend on the cloning of particular nucleic acid molecules. Indeed it is possible to create a whole genome array on a 1 mm$^2$ grid by arranging, for example, rows of parallel, elongated single stranded nucleic acid molecules. Each row contain, for example 3000 nucleic acid molecules, each about 10,000 bases long (or about 7 î long). Assuming a reasonable spacing between rows and between molecules in a single row, about such 100 rows could be held on a 1 mm$^2$ grid. Thus, such a grid could contain an entire genome or $3 \times 10^9$ bases (100 rows×3000 molecules/row×10,000 bases/molecule). Such an arrangement could make it possible to analyze one genome equivalent of sequence per day (assuming $3 \times 10^5$ bases analyzed/image×10,000 images/day).

Arrays can be produced by adsorbing thiolated nucleic acid molecules an array of gold dots. For example, gold dots having a diameter of less than 1 nm (e.g., 2, 5, 10, 50, 100 nm) can be regularly aligned on a carbon film as a rectangular lattice with 10, 20, 50, 100, 200, 300 400 or 500 nm spacing or any other desirable spacing.

A reusable addressable array can be constructed by binding each of a plurality of short, specific oligonucleotides to a specific position on a surface, e.g., to a specific gold dot in an array of such dots. Each oligonucleotide would hybridize to a specific single-stranded sequence thus creating an array of nucleic acid molecules at known locations.

The references cited herein and are hereby incorporated by reference in their entirety.

A number of embodiments of the invention have been described. Nevertheless, it will be understood that various modifications may be made without departing from the spirit and scope of the invention. Accordingly, other embodiments are within the scope of the following claims.

The invention claimed is:

1. A method for determining the sequence of a plurality of bases in a nucleic acid molecule, comprising:
   (a) providing a support surface bearing a nucleic acid molecule having a single stranded region;
   (b) exposing the nucleic acid molecule to four different base-specific nucleotides in the presence of an organic solvent, wherein each of the four different base-specific nucleotides comprises a different element having an atomic number greater than 25 and each element having an atomic number greater than 25 differs in atomic number from each other element having an atomic number greater than 25 by an atomic number of at least 15;
   (c) allowing the four different base-specific nucleotides to form base-pairs with bases in the single stranded region of the nucleic acid molecule;
   (d) removing at the non-base paired base-specific nucleotides by washing;
   (e) detecting the base paired nucleotides by electron microscopy; and
   (f) analyzing the detected base paired nucleotides to determine the sequence of a plurality of bases in the nucleic acid molecule.

2. The method of claim 1 wherein the elements are selected from the group consisting of: Pt, Eu, Pd, Co, U, Os, Fe, Hg, Gd, Cd, Zn, Ac, W, Mo, and Mn.

3. The method of claim 1 wherein the four different base-specific nucleotides consist of:
   (i) a label comprising a substituted adenine,
   (ii) a label comprising a substituted uracil or a substituted thymine,
   (iii) a label comprising a substituted cytosine, and
   (iv) a label comprising a substituted guanine.

4. The method of claim 1 wherein the four elements are: (i) Pt, Eu, Pd, and Co; (ii) U, Os, Pd and Fe; (iii) Hg, Gd, Cd and Zn; or (iv) Ac, W, Mo and Mn.

5. The method of claim 3 wherein N7 or N9 of the substituted adenine is substituted with a group comprising an element having an atomic number greater than 25.

6. The method of claim 3 wherein N7 or N9 of the substituted guanine is substituted with a group comprising an element having an atomic number greater than 25.

7. The method of claim 3 wherein N1 of the substituted cytosine is substituted with a group comprising an element having an atomic number greater than 25.

8. The method of claim 3 wherein N1 of the substituted uracil is substituted with a group comprising an element having an atomic number greater than 25.

9. The method of claim 3 wherein N1 of the substituted thymine is substituted with a group comprising an element having an atomic number greater than 25.

10. The method of claim 3 wherein the substituted adenine has a substitution that increases the specificity of Watson-Crick type base-pairing with uracil or thymine.

11. The method of claim 3 wherein the substituted thymine or substituted uracil has substitution that increases the specificity of Watson-Crick type base-pairing with adenine.

12. The method of claim 3 wherein the substituted cytosine has a substitution that increases the specificity of Watson-Crick type base-pairing with guanine.

13. The method of claim 3 wherein the substituted guanine has a substitution that increases the specificity of Watson-Crick type base-pairing with cytosine.

14. The method of claim 10 wherein the substituted adenine is substituted at C2 or C8 or both C2 and C8.

15. The method of claim 11 wherein the substituted thymine or the substituted uracil has a substitution at C5 or C6 or both C5 and C6.

16. The method of claim 12 wherein the substituted cytosine or the substituted uracil has a substitution at C5 or C6 or both C5 and C6.

17. The method of claim 10 wherein the substituted guanine is substituted at C2.

18. The method of any of claims 14-17 wherein the modification is a substituted or unsubsituted alkyl group or a halogen.

19. The method of claim 1 wherein the 3' nucleotide or the 5' nucleotide of the nucleic acid molecule is covalently bound to a defined region of the support surface.

20. The method of claim 19 wherein the defined region of the support surface is coated with gold.

21. The method of claim 1 wherein the support surface bears a plurality of nucleic acid molecules having a single stranded region wherein the 3' nucleotide or the 5' nucleotide of each nucleic acid molecule is covalently bound to a defined region of the support surface.

22. The method of claim 21 wherein each of the plurality of nucleic acid molecules having a single stranded region is covalently bound to a different defined region of the support surface.

23. The method of claim 1 wherein each base-specific nucleotide comprises at least two atoms having an atomic number greater than 25.

24. The method of claim 23 wherein each base-specific nucleotide comprises a group selected from the group consisting of: $B_{10}I_9COOH$, $C_2B_{10}I_{10}$, $C_2B_{10}Br_{10}$, $C_2B_{10}Cl_{10}$, $C_2B_{10}F_{10}$.

25. The method of claim 1 wherein in the electron microscopy is transmission electron microscopy.

26. The method of claim 25 wherein the transmission electron microscopy includes the use of a transmission electron microscope comprising a Zernike phase plate located behind the objective lens.

27. The method of claim 1 wherein the electron microscopy comprises the use of a complex electron microscope.

28. The method of claim 22 wherein the plurality of nucleic acid molecules form a regular array.

29. The method of claim 1 wherein each base-specific label comprises two or more atoms having an atomic number greater than 25.

30. The method of claim 1 wherein each base-specific label comprises three or more atoms having an atomic number greater than 25.

31. The method of claim 1 wherein each base-specific label comprises four or more atoms having an atomic number greater than 25.

32. The method of claim 1 wherein each base-specific label comprises five or more atoms having an atomic number greater than 25.

33. The method of claim 1 wherein each base-specific label comprises six or more atoms having an atomic number greater than 25.

34. The method of claim 1 wherein each base-specific label comprises seven or more atoms having an atomic number greater than 25.

35. The method of claim 1 wherein each base-specific label comprises eight or more atoms having an atomic number greater than 25.

36. The method of claim 1 wherein each base-specific label comprises nine or more atoms having an atomic number greater than 25.

37. The method of claim 1 wherein each base-specific label comprises ten or more atoms having an atomic number greater than 25.

* * * * *

UNITED STATES PATENT AND TRADEMARK OFFICE
CERTIFICATE OF CORRECTION

PATENT NO. : 7,419,833 B2
APPLICATION NO. : 10/424682
DATED : September 2, 2008
INVENTOR(S) : Kuniaki Nagayama It is certified that error appears in the above-identified patent and that said Letters Patent is hereby corrected as shown below:

On the Title Page, Col. 2 (Other Publications), Line 27, delete "Cytostine-" and insert -- Cytosine --.

On the First Page, Col. 2 (Other Publications), Line 30, delete "Conversino" and insert -- Conversion --.

In Column 14, Line 17, in claim 1, delete "removing at the" and insert -- removing the --.

In Column 14, Line 58 (approx.), in claim 11, delete "has substitution" and insert -- has a substitution --.

In Column 15, Line 11, in claim 18, delete "unsubsituted" and insert -- unsubstituted --.

Signed and Sealed this

Fourth Day of August, 2009

JOHN DOLL
*Acting Director of the United States Patent and Trademark Office*